United States Patent
Mohl

(10) Patent No.: US 7,331,922 B2
(45) Date of Patent: Feb. 19, 2008

(54) METHOD AND DEVICE FOR THE INTERMITTENT OCCLUSION OF THE CORONARY SINUS

(76) Inventor: Werner Mohl, Hafnerberg 66, A-2571, Altenmarkt/Thennenberg (AT)

( * ) Notice: Subject to any disclaimer, the term of this patent is extended or adjusted under 35 U.S.C. 154(b) by 383 days.

(21) Appl. No.: 10/484,194

(22) PCT Filed: Jul. 17, 2002

(86) PCT No.: PCT/AT02/00212
§ 371 (c)(1),
(2), (4) Date: Apr. 28, 2004

(87) PCT Pub. No.: WO03/008018
PCT Pub. Date: Jan. 30, 2003

(65) Prior Publication Data
US 2004/0172004 A1 Sep. 2, 2004

(30) Foreign Application Priority Data
Jul. 17, 2001 (AT) .............................. A 1113/2001

(51) Int. Cl.
*A61M 1/10* (2006.01)
(52) U.S. Cl. ............................ 600/17; 600/67; 600/151
(58) Field of Classification Search .................... None
See application file for complete search history.

(56) References Cited

U.S. PATENT DOCUMENTS

| 4,493,697 A | 1/1985 | Krause et al. |
|---|---|---|
| 4,689,041 A | 8/1987 | Corday et al. |
| 4,934,996 A | 6/1990 | Mohl et al. |
| 4,969,470 A | 11/1990 | Mohl et al. |
| 5,024,668 A | 6/1991 | Peters et al. |
| 5,033,998 A * | 7/1991 | Corday et al. ................. 600/18 |
| 5,505,698 A | 4/1996 | Booth et al. |
| 6,090,096 A * | 7/2000 | St. Goar et al. ............ 604/509 |
| 6,458,323 B1 * | 10/2002 | Boekstegers ................. 422/44 |

* cited by examiner

*Primary Examiner*—Kristen D. Mullen
(74) *Attorney, Agent, or Firm*—Nixon & Vanderhye P.C.

(57) ABSTRACT

A method and apparatus are provided for the intermittent occlusion of a coronary sinus. The method includes occluding the coronary sinus with an occlusion device, continuously measuring the fluid pressure in the occluded coronary sinus and defining measured pressure by use, releasing the occlusion of the coronary sinus as a function of at least one parameter derived from the measured pressure values, introducing a perfusate into the occluded coronary sinus or at least a vein running into the coronary sinus, and controlling an amount of perfusate introduced as a function of the at least one parameter derived from the measured pressure values. The at least one parameter may be a derivative of a fluid pressure curve according to time, and/or a plateau value of the pressure minima, and/or a pressure value of the pressure maxima, of consecutive heartbeats that is computationally estimated from the measured fluid values.

37 Claims, 10 Drawing Sheets

METHOD AND DEVICE FOR THE INTERMITTENT OCCLUSION OF THE CORONARY SINUS

This application is the U.S. national phase of international application PCT/AT02/00212 filed Jul. 17, 2002 which designated the U.S., the entire contents of which are hereby incorporated by reference.

The invention relates to a method for the intermittent occlusion of the coronary sinus, in which the coronary sinus is occluded by an occlusion device, the fluid pressure in the occluded coronary sinus is continuously measured and the occlusion of the coronary sinus is released as a function of at least one parameter derived from the measured pressure values, as well as a device for the intermittent occlusion of the coronary sinus.

Arterial blood, which feeds the heart muscle, is able to pass through healthy heart tissue to nourish the same, yet has difficulty in reaching ischemic tissue. As a result, the supply of nutrients to ischemic tissue and the discharge of metabolic degradation products from ischemic tissue are hampered. In this context, it has already been proposed to supply ischemic tissue with blood by retrograde perfusion. The retroinfusion of blood in coronary veins plays an important role particularly in the field of myocardial protection during a short-term coronary artery occlusion at a cardiologic intervention. A typical intervention of this type is, for instance, the balloon dilatation of an arteriosclerotically constricted coronary artery. In that method, which is also known as percutaneous transluminal coronary angioplasty (PTCA), a balloon catheter is conducted into the region of the stenosis of the coronary artery under X-ray monitoring and the arteriosclerotic plaque is compressed by inflating the balloon attached to the end of the catheter. During the dilatation of the balloon no supply with oxygen-containing blood of the tissue takes place downstream in the artery, functional modifications in the ischemic zone of the myocardium being observable already at dilatations lasting longer than 30 seconds. Analogous problems in respect to the ischemic protection of the myocardium will also be faced in other interventions for coronary vascularization such as, e.g., atherectomies, coronary endoprostheses and laser applications.

In connection with a short-term ischemic protection, a retroinfusion of arterial blood or other nutritive liquids into a vein of the respective ischemic region of the myocardium has been practiced for some time. In doing so, the blood is pumped through the respective vein into the nutritive capillaries of the ischemic region, thus supplying the myocardium with oxygen and substrates in that region. A device for the retroinfusion of coronary veins by which a pressure-controlled intermittent coronary sinus occlusion can be carried out is, for instance, known from U.S. Pat. No. 4,934,996. That device comprises a means for occluding the sinus, such as, e.g., an inflatable balloon catheter, a pressure measuring means for measuring the fluid pressure within the coronary sinus and a control means for generating trigger signals to trigger or release an occlusion. The control means is designed in a manner that the pressure maximum during each heartbeat is measured in the coronary sinus, a plateau value of the pressure maxima of consecutive heartbeats is computationally estimated and the occlusion of the coronary sinus is released on the basis of the plateau value of the pressure maxima.

The occlusion of the coronary sinus causes a pressure increase and, consequently, a retroperfusion of blood via the respective vein into the nutritive capillaries of the ischemic region so as to enable the supply of nutrients to those regions. At a release of the occlusion the retroperfused blood is scoured while the metabolic waste products are simultaneously carried off. In the method according to U.S. Pat. No. 4,934,996, a systolic pressure curve is, thus, computationally estimated on grounds of the pressure maximum measured in the coronary sinus during each heartbeat, whereby the intermittent occlusion is controlled as a function of the plateau value of the systolic pressure curve. From the course of the estimated systolic pressure curve, also the efficiency of the heart may be concluded, the slope of the curve reflecting, for instance, the contractibility of the heart. The slope of the curve does, of course, also influence the level of the plateau value with a lower plateau value being reached at a flatter curve, the plateau, moreover, being reached after an extended period of time following the start of occlusion as compared to a healthy heart. A displacement of the curve will also result, if a coronary vessel is closed either temporarily at an interventional action like PTCA or stenting or even for an extended period due to a complication, so that the pressure curve will rise more slowly and also need more time to reach the plateau.

The present invention aims to provide a method and device for the intermittent occlusion of the coronary sinus, by which the sufficient retrograde supply of the ischemic region with blood will be safeguarded even at a change in the pressure curve on account of the occlusion of a coronary vessel. Furthermore, an intervention longer than with the known devices is to be set also on the arterial side without involving any tissue infarcts in the affected myocardial regions. The diagnostic component of an intermittent occlusion known, for instance, from U.S. Pat. No. 4,887,608 is to be maintained.

To solve this object, the method according to the invention essentially consists in that a perfusate is introduced into the occluded coronary sinus or at least a vein running into the coronary sinus, wherein the control of the introduced amount of perfusate is performed by considering at least one parameter derived from the measured pressure values. The device according to the invention includes an occlusion means for the occlusion of the coronary sinus, a control means for the triggering or release of said occlusion and a pressure measuring means for the determination of the fluid pressure prevailing in the coronary sinus during the occlusion, and is characterized in that a duct capable of being introduced into the coronary sinus, or a vein running into the coronary sinus, and charged with a perfusate as well as a perfusate pump connected with an automatic controller are provided, that the pressure measuring means comprises a memory for the measured pressure values and is connected with a computation unit for the calculation of at least one parameter derived from said measured pressure values, wherein the control of the introduced amount of perfusate is performed under consideration of said parameter derived from the measured pressure values.

In accordance with the invention, a perfusate is introduced during the occlusion into the occluded coronary sinus, or at least a vein running into the coronary sinus, with the control of the introduced amount of perfusate being performed under consideration of at least one parameter derived from the measured pressure values. By the introduction of a perfusate, the pressure deficit caused by a temporary or even extended occlusion of a coronary vessel due to interventional actions like PTCA or stenting, or due to complications, is recompensated. As a result, the systolic or diastolic pressure curve, which has flattened due to the occlusion of the coronary vessel, can be raised again such that the pressure level will correspond to a normal or set value and sufficient retroperfusion into the ischemic region will be ensured. The introduced amount of perfusate must be controlled in a manner that the retroinfusion rate will be neither too low nor too high. At too low a retroinfusion rate, the venous pressure would be too low to ensure sufficient supply of oxygen to the myocardium and enable the maintenance of the myocardial function in the ischemic region. Too high an infusion rate, i.e. too high a coronary venous pressure would, however, entail the risk of an overperfusion, which would not enhance the retrograde nutritive capillary filling but rather impede the contraction of the myocardium and lead to an ineffective flow-off of the arterial blood into the systematic circulation. Retroinfusion at too high a coronary venous pressure, moreover, would entail the risk of causing irreversible damage to the vessel walls.

The automatic control of the amount of perfusate is performed as a function of at least one parameter derived from the measured pressure values with a number of options being conceivable in this respect. Thus, it is, for instance, feasible to preset fixed limit values for the individual measured pressure values and no longer increase the amount of introduced perfusate upon exceeding of these limit values. The local maxima of the measured pressure values of consecutive heartbeats rise within the occluded coronary sinus in accordance with an exponential curve while approaching a plateau value, so that it will be difficult to indicate a control variable that is independent of the respective absolute pressure prevailing in the occluded coronary sinus. It is, therefore, advantageously proceeded in a manner that the derivation of the fluid pressure curve according to time is chosen as said parameter derived from the measured pressure values. In this case, the device is further developed such that the measured pressure values stored in the memory are assigned time stamps and the memory is connected with the computation unit for the calculation of the derivation of the fluid pressure curve according to time. Thus, a control variable is preset, which enables the control of the introduced amount of perfusate independently of the respective absolute pressure value. The time-dependent derivation of the pressure curve reflects the slope of the pressure curve and indirectly allows a statement as to the instantaneous pressure level and the speed of the pressure increase within a heartbeat, so that the perfusion rate will have to be increased at an insufficient rise of the pressure curve in order to reach values corresponding to those of a healthy heart and allowing a compensation of the arterial blood flow deficit caused by the occlusion of a coronary vessel. The consideration of the time-dependent derivation of the pressure curve as a control variable is also advantageous because it enables the optimum adjustment of the occlusion time. As in contrast to other retroperfusion methods, it is the occlusion time which constitutes the regulated variable in the mode of control according to the invention rather than the internal pressure of a vessel. It is, thus, to be ensured that the internal pressure of the vessel will have reached a plateau value when reaching the envisaged occlusion time.

In the context of the invention, it may preferably also be proceeded in a manner that the local maximum and/or local minimum each occurring within a heartbeat, of the derivation of the fluid pressure curve according to time is chosen as said parameter derived from the measured pressure values. In this case, the device is further developed such that the computation unit comprises a comparator circuit for the determination of the local maximum and/or local minimum each occurring within a heartbeat, of the derivation of the fluid pressure curve according to time, whereby the control of the introduced amount of perfusate is performed as a function of the local maxima and/or local minima. The local maximum or local minimum, respectively, of the time-dependent derivation allows for a precise description of the pressure curve and, in particular, the slope of the pressure increase or decrease, respectively, so that also this parameter is perfectly suitable for the control of the introduced amount of perfusate. The amount of data to be processed and evaluated by the automatic controller is thereby reduced while nevertheless obtaining a precise curve description. Further processing is feasible in that the plateau value of the local maxima, and/or the plateau value of the local minima, of the derivation of the fluid pressure curve according to time are chosen as said parameter derived from the measured pressure values. The device in this case is further developed such that the computation unit comprises an evaluation circuit which computationally estimates a plateau value of the local pressure maxima and/or local pressure minima of the derivation of the fluid pressure curve according to time and cooperates with the pump for the control of the introduced amount of perfusate as a function of the plateau value. This preferred mode of control is, thus, based on the plateau value of the extreme values of the time-dependent derivation of the pressure curve, which plateau value is substantially reached at the same time at which the systolic or diastolic pressure curve, respectively, reaches a plateau value. The plateau value in this case is constantly estimated by computation on grounds of the current pressure values.

Controlling is preferably performed in that the local maxima and/or local minima of the derivation of the fluid pressure curve according to time, and/or the plateau values thereof, are compared with a set value. The device in this case is further developed such that the computation unit comprises a comparator circuit for the comparison of the local maxima and/or local minima of the derivation of the fluid pressure curve according to time, and/or the plateau values thereof, with a stored set value. The set value may, for instance, be a value corresponding to that of a healthy heart or a value measured in the affected patient prior to the intervention.

According to another embodiment of the invention, the time-dependent derivation of the pressure curve may be replaced or supplemented with another parameter derived from the measured pressure values, to which end it is proceeded in a manner that a plateau value of the pressure minima, and/or a plateau value of the pressure maxima, of consecutive heartbeats is computationally estimated from the measured fluid values and used as said parameter for the control of the introduced amount of perfusate. The device in this case is designed in a manner that the pressure measuring means comprises a memory for local maxima of the measured pressure values and the computation unit comprises an evaluation circuit computationally estimating a plateau value of the pressure maxima of consecutive heartbeats and cooperates with the pump for the control of the introduced amount of perfusate as a function of the plateau value of the pressure maxima. The plateau values in this case can be readily estimated on the basis of the measured values of the pressure minima and pressure maxima, respectively, the computational estimation of the plateau values being preferably performed by inserting the pressure maxima or minima into an exponential curve. The estimation of the respective plateau value is, thus, based on a mathematical approximation method, with the plateau value being newly calculated at every heartbeat on grounds of the measured pressure values. If the systolic pressure curve is raised by the additional introduction of perfusate, the diastolic pressure curve will naturally rise too, with a plateau value being reached both for the pressure maxima and for the pressure minima in both cases after a certain period of time. If the infusion flow of the perfusate is chosen too high, a disproportionately strong increase in the plateau value of the diastolic pressure curve relative to the systolic pressure curve will result, so that is appears advantageous on account of these findings that the control of the introduced amount of perfusate is performed by taking into account the measured values for the pressure minima and the pressure maxima.

It is, thus, feasible to calculate not only the systolic plateau but also the diastolic plateau and evaluate the trend of the two pressure curves relative to each other in order to determine the respective optimum of the occlusion time as well as the retrograde infusion flow. If the optimum perfusion rate is exceeded, the plateau value for the pressure maxima will, as a rule, remain constant, whereas the plateau value of the pressure minima will rise further. With this in mind, the control of the introduced amount of perfusate is preferably performed in a manner that the difference of the plateau values of the pressure minima and pressure maxima is calculated and the amount of perfusate introduced is raised until the difference remains constant or increases. In this context, the device is further developed such that the control means comprises a comparator circuit for the comparison of the plateau values of the pressure minima and pressure maxima and cooperates with the pump for the control of the introduced amount of perfusate as a function of the difference between the pressure maxima and pressure minima, whereby the amount of perfusate introduced is raised as long as the difference remains constant or increases. The perfused fluid flow thus slowly rises until the difference between the plateau values of the pressure minima and the pressure maxima remains constant or increases. If and when this is no longer the case, the optimum perfusion rate has been reached and the introduced amount of perfusate is, therefore, kept constant.

As already mentioned, the pressure deficit caused by a coronary vessel occlusion is compensated by the additional introduction of a perfusate into the occluded coronary sinus in order to raise both the systolic and the diastolic pressure curves. This ensures a sufficient retrograde supply of blood to the ischemic region and further offers the advantage that an extended intervention can be set on the arterial side, which would otherwise be impossible on account of the loss of too large a perfusion portion.

In addition to the control of the introduced amount of perfusate, also the optimum determination of the occlusion times is of relevance, and in this context it is proceeded in a manner that the pressure maxima of consecutive heartbeats are compared with the plateau value of the pressure maxima and the occlusion of the coronary sinus is released upon reaching of a predetermined percentage of the plateau value of the pressure maxima, said percentage preferably being chosen larger than 70 and smaller than 98. The device in this respect is preferably further developed such that the automatic controller is connected with the control means for the triggering and release of the occlusion by the occlusion device, wherein the occlusion is released as the pressure maxima of consecutive heartbeats have reached a predetermined percentage of the plateau value of the pressure maxima, said percentage being larger than 70 and smaller than 98.

In a preferred manner, the perfusate can be supplemented with pharmaceuticals. Such pharmaceuticals may, for instance, be agents for the dissolution of thrombi as well as therapeutically or diagnostically active substances such as, e.g., coagulation inhibitors, contrast agents or beta-blockers.

In a preferred manner, the perfusate is directly introduced into the region of the vessels to be activated, to which end the duct to be charged with a perfusate is arranged so as to be displaceable relative to the occlusion device and capable of being pushed forward directly into the region of the vessels to be activated. The perfusate can thus be selectively introduced on the desired site, so that it will be feasible to overcome the ventricular pressure directly in the jeopardized area, i.e. in the region to be activated. In this context it appears advantageous to provide a local separation between the perfusate introduction and the occlusion device. The perfusion catheter can, for instance, be pushed forward as far as into the coronary vein circulation with the perfusion being effected as a function of the perfusion resistance. The pressure measurement is advantageously carried out in the region of the occlusion device so that a local separation between the pressure measurement and the perfusate introduction will be obtained, thus avoiding any influence of the pressure measurement.

An optimization and/or further control in the context of the invention may preferably be realized in that the fluid pressure in an arterial heart vessel is additionally measured and the control of the introduced amount of perfusate is effected by additionally considering the arterial pressure values measured, or that an additional pressure measuring means is provided for the determination of the fluid pressure in an arterial heart vessel and the additional pressure measuring means is connected with the computation unit, whereby the control of the introduced amount of perfusate is effected under additional consideration of the arterial pressure values measured. This enables the introduced amount of perfusate to be controlled in the manner of a closed loop, the extended closed loop opening up additional diagnostic and control options.

Basically, the control means, the computation unit and the automatic controller may constitute separate structural units in respect to the device according to the invention, yet the control means may alternately comprise the automatic controller for the pump and/or the computation unit.

In the following, the invention will be explained in more detail by way of a drawing. Therein, FIG. 1 is a diagrammatic view of a heart comprising a device for the intermittent occlusion of the coronary sinus, FIGS. 2 and 3 are comparative illustrations of the heart tissue, FIGS. 4 and 5 are graphs of the coronary sinus pressure course, FIG. 6 illustrates the course of the pressure plateau, FIG. 7 illustrates the course of the pressure rise time, FIG. 8 is a section through the distal end of a catheter plus expanded balloon intended for application, FIG. 9 is a section through the expanded balloon along line IX-IX of FIG. 8, and FIG. 10 illustrates a modified configuration sectioned along line X-X of FIG. 8.

FIG. 1 schematically illustrates a device for the intermittent occlusion of the coronary sinus, showing a multilumen catheter 1 whose distal end 2 is inserted in the coronary sinus of the heart 3 via the atrium. The proximal end 4 of the catheter 1 has a balloon inflation lumen 5 connected with a pump 6. The pressure prevailing at the distal end 2 of the catheter 1 is determined by a pressure measuring means 7, which also includes a memory for the measured values determined. The respectively measured pressure values are fed to a control means 8 comprising a circuit for delivering control signals via duct 9 to start and stop the pump 6. The pressure measuring means 7 is further connected with an automatic controller 10 that serves to control a further pump 11 and adjust the amount of perfusate delivered by the pump 11 via a further lumen 12 of the catheter 1.

FIG. 2 is a comparative illustration of the condition of the heart tissue in different situations. FIG. 2a depicts the normal situation, in which the heart tissue 13 is sufficiently supplied from the arterial side 14 via arteries 15, 16 and 17. The veins are schematically indicated by 18, 19 and 20. FIG. 2b illustrates an ischemic state in which the central artery 16 is closed or constricted. The pertinent tissue region is supplied with blood to an insufficient degree or not at all. No retrograde perfusion into the ischemic area takes place. FIG. 2c illustrates the situation that results from the application of the invention. The artery 16 is again closed such that no sufficient supply of the respective tissue part would be provided. Yet, blood is retroinfused into the ischemic area from the venous side as schematically indicated by arrow 21, the occlusion of the vein being schematically shown at 22.

FIG. 3 is an enlarged illustration according to FIG. 2c, from which the pressure course within the vein as well as the reflux of the retroinfused blood into the ischemic area, which increases with pressure, are apparent. The closed artery 16 and the vein 19 via which the perfusate enters the tissue in the sense of arrow 21 are visible again. During the occlusion, the pressure course represented on the right-hand side of FIG. 3 will be measured in the occluded vein, the amount of ischemic area reached increasing with the level of the pressure maxima increasing.

FIG. 4 depicts the pressure course detected by the measuring means 7, the start of the occlusion being shown at T0. A series of systolic pressure peaks 23 and a series of diastolic troughs 24 are visible. The pulse period 25 of the heartbeat is illustrated by the time between consecutive peaks or consecutive troughs. The systolic pressure peaks can be inserted in an exponential curve 26 of the formula $Ps(t)=As(1-e^{-t/Ts})$, where As represents the asymptotic plateau of the pressure maxima and Ts is the time that expires until the plateau is reached. Similarly, the diastolic pressure troughs can be inserted in an exponential curve 27 of the formula $Pd(t)=Ad(1-e^{-t/Td})$, where Ad represents the asymptotic plateau of the pressure troughs and Td is the time that expires until the plateau is reached. On the assumption that the systolic and diastolic pressure curves 26 and 27 represented in FIG. 4 correspond to those of a healthy heart or to set values, flatter curve courses may be indicated as shown at 28 and 29, which correspond to that situation in which a coronary vessel is closed temporarily at an interventional action or even longer due to a complication. It is apparent that the plateau values of curves 28 and 29 are lower with the plateau being reached after a longer period of time. By the introduction of additional perfusate into the occluded coronary sinus as in accordance with the invention, curves 28 and 29 are to be raised to the levels of curves 26 and 27 such that a sufficient retrograde supply of the target area will be safeguarded.

FIG. 5 merely depicts the systolic pressure curve 16, wherein it is apparent that the curve of the local pressure maxima drops back to the base level at a release of the occlusion at $t_1$ until that point of time $t_2$ at which the occlusion is initiated again, whereupon the cycle will be repeated.

In FIG. 6, the course of the pressure plateau is illustrated over the total period of an intervention at a coronary artery. The course of the systolic pressure plateau is denoted by 30 and the course of the diastolic pressure plateau is denoted by 31, the intervention being terminated and the occlusion of the coronary artery being released at point 32.

Figure 1:
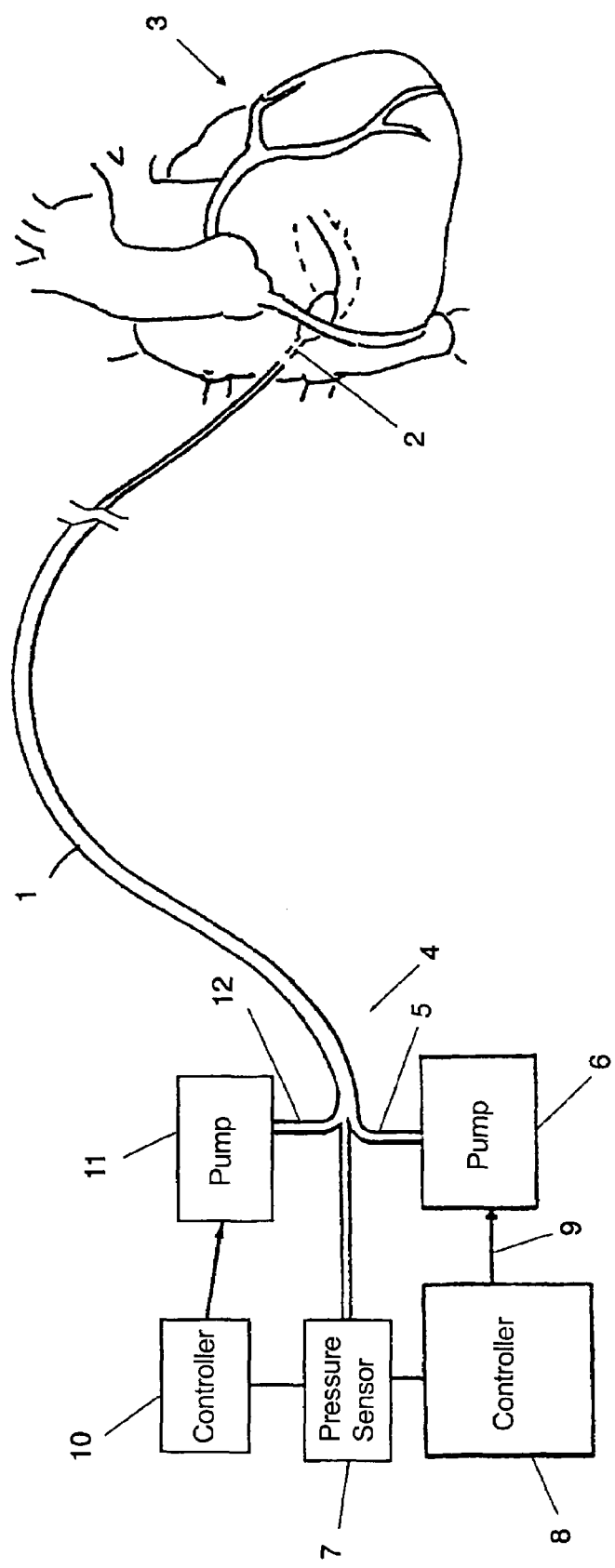
Figure 2:
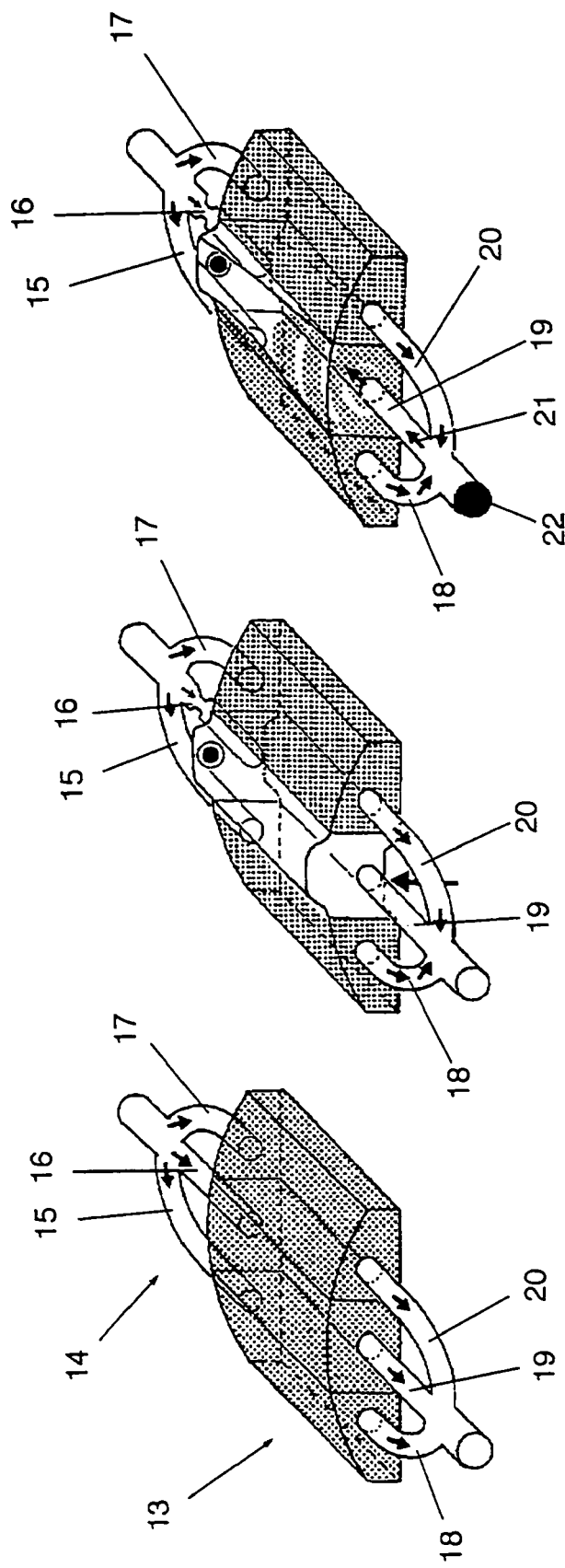
Figure 3:
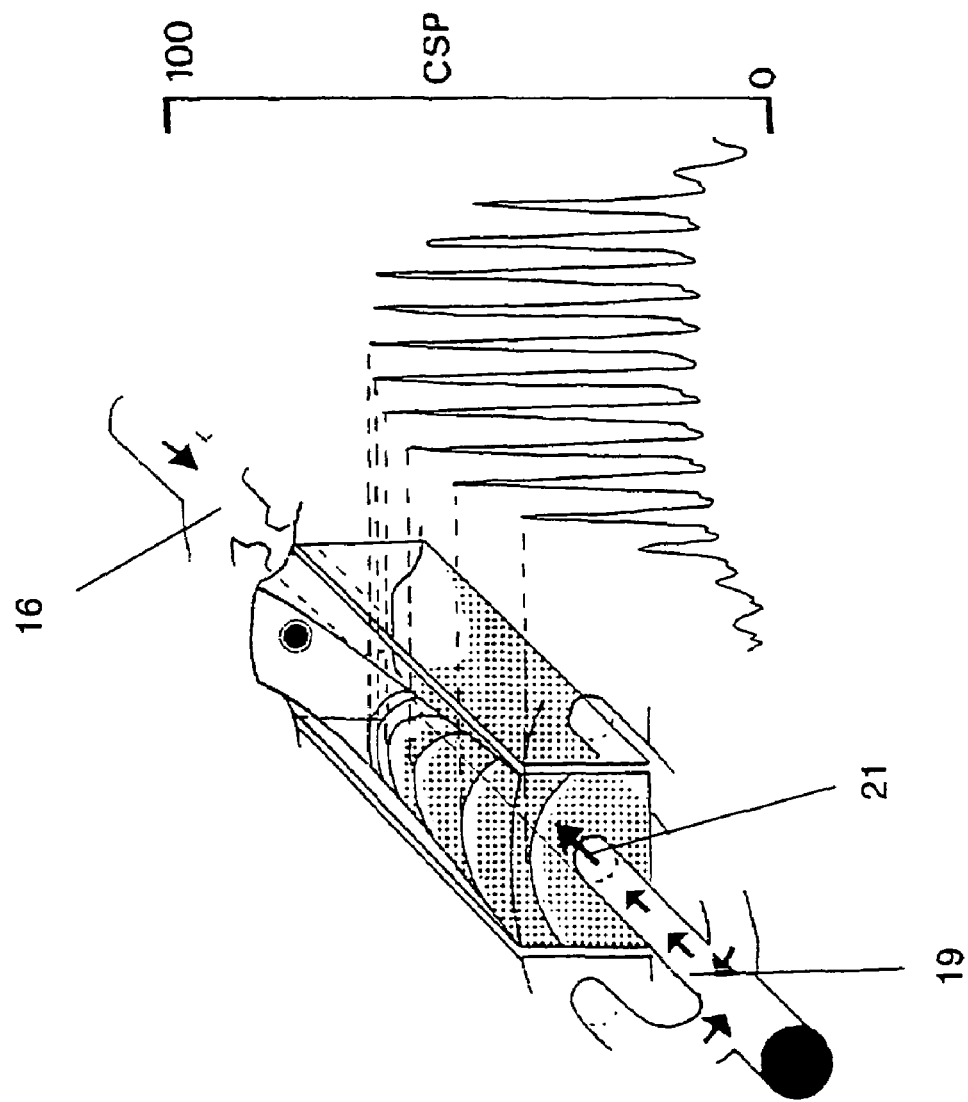
Figure 4:
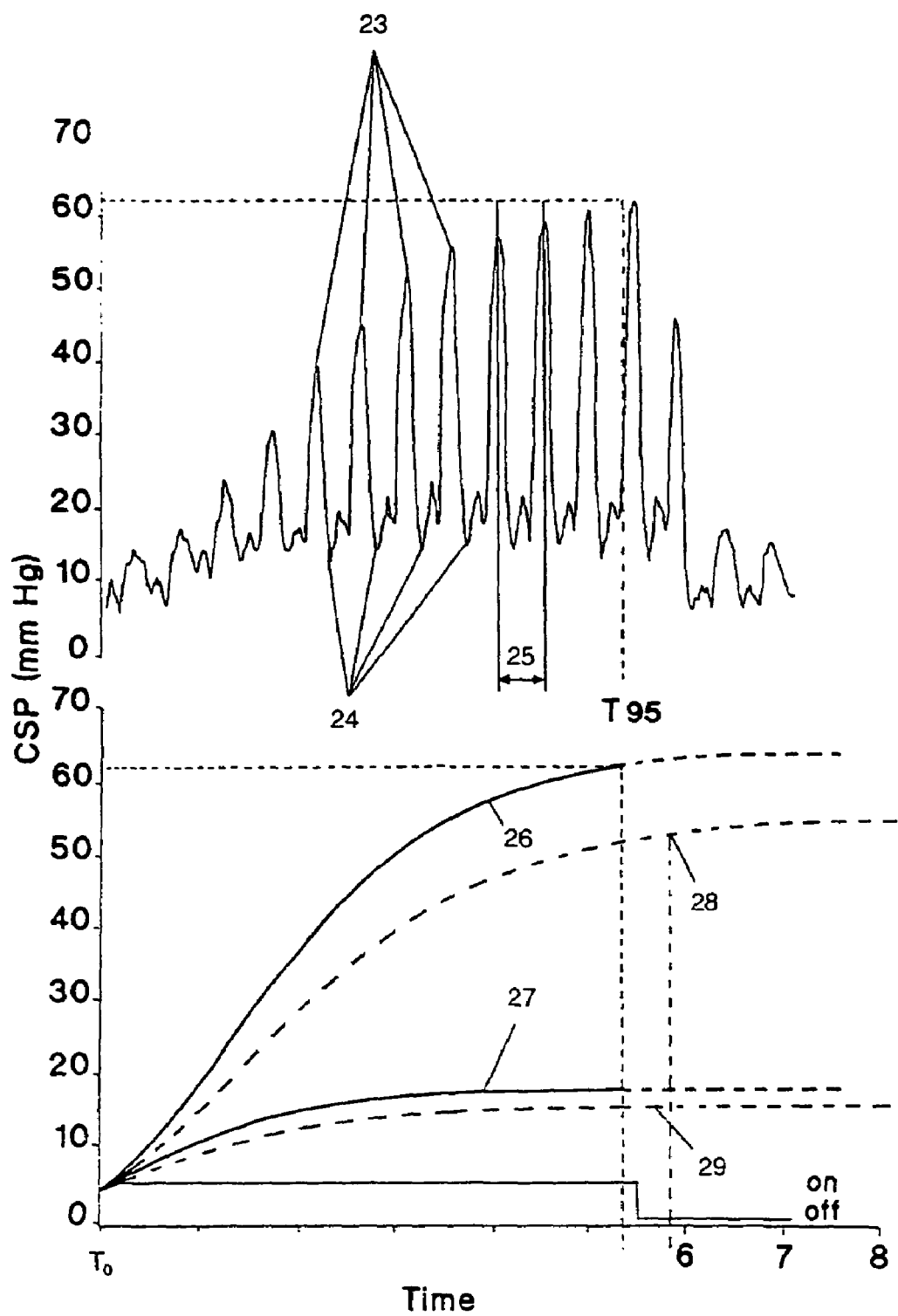
Figure 5:
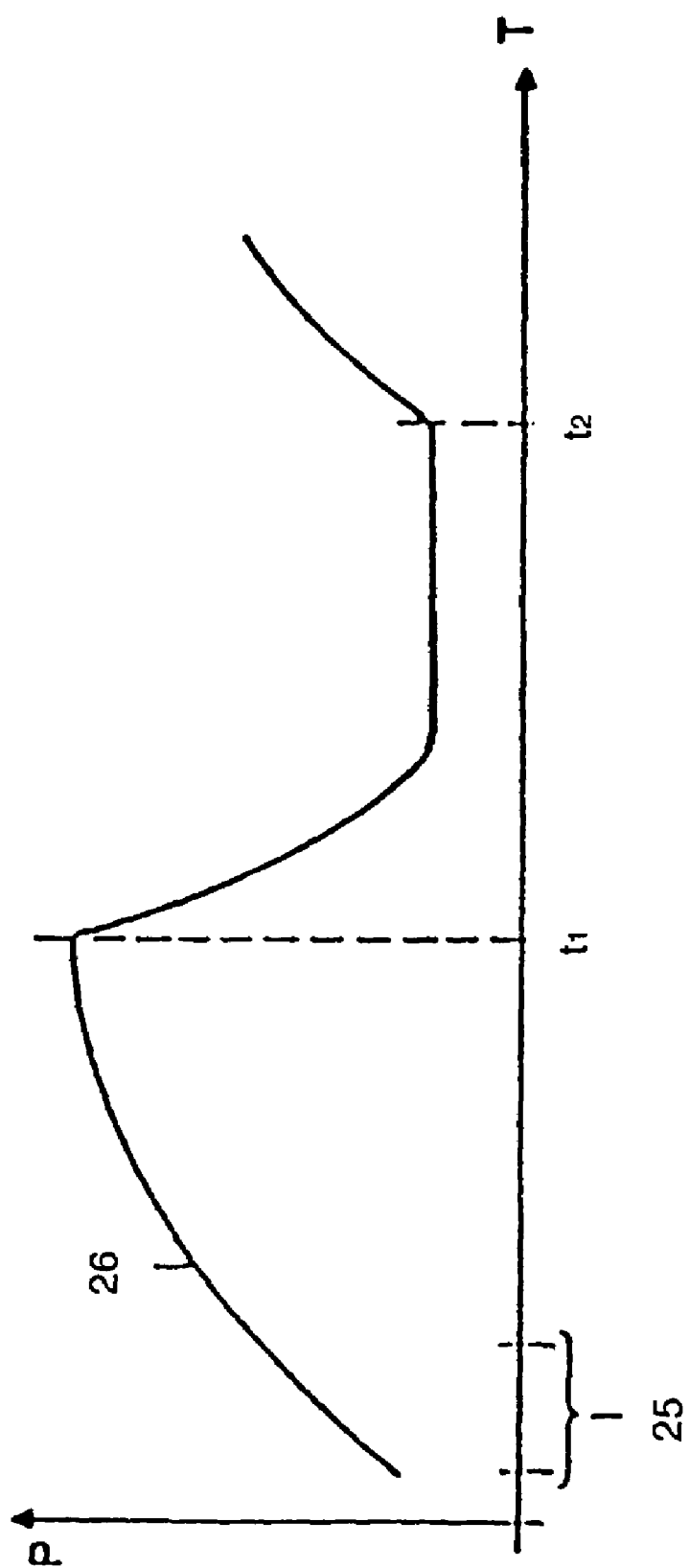
Figure 6:
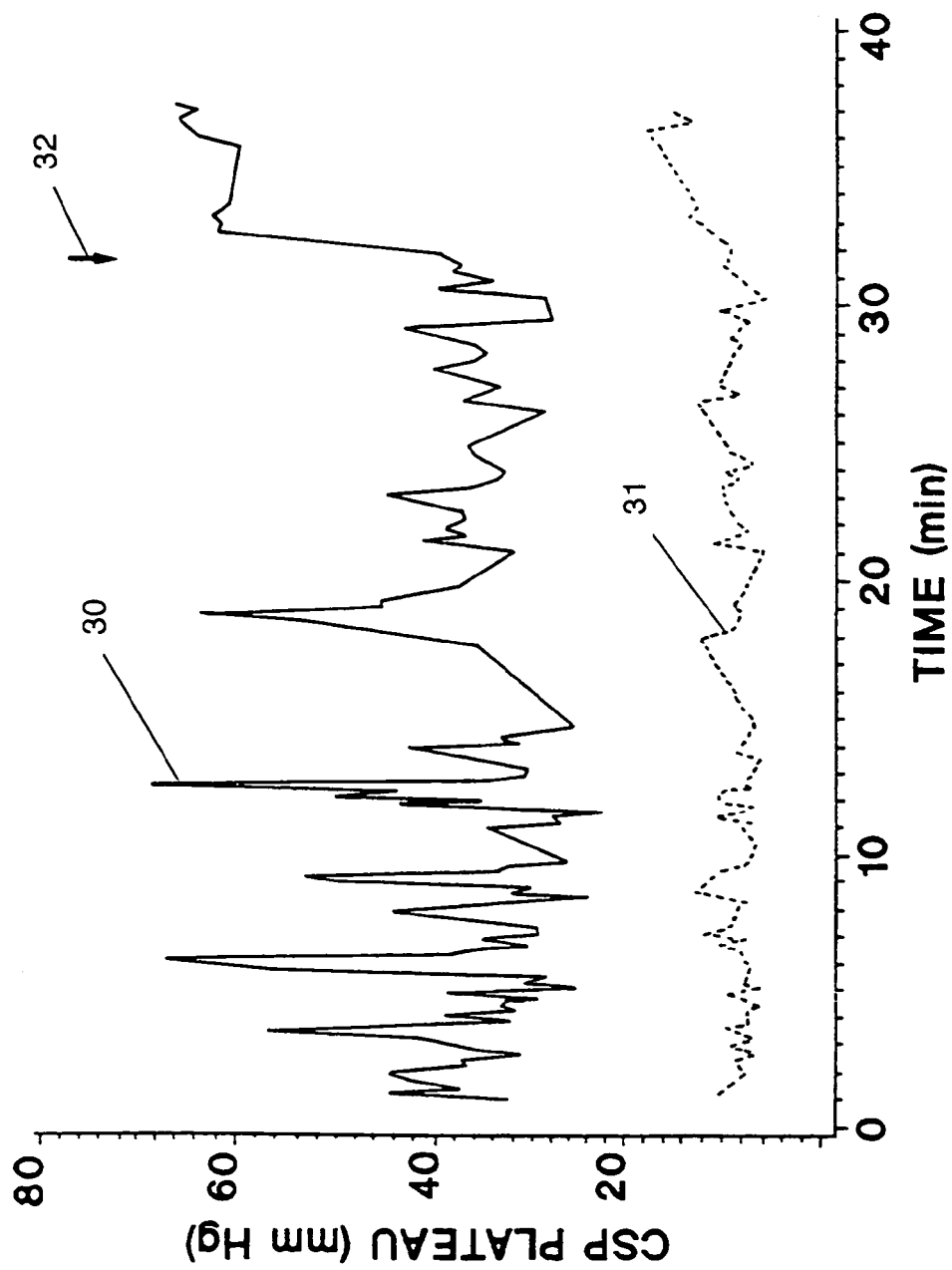
Figure 7:
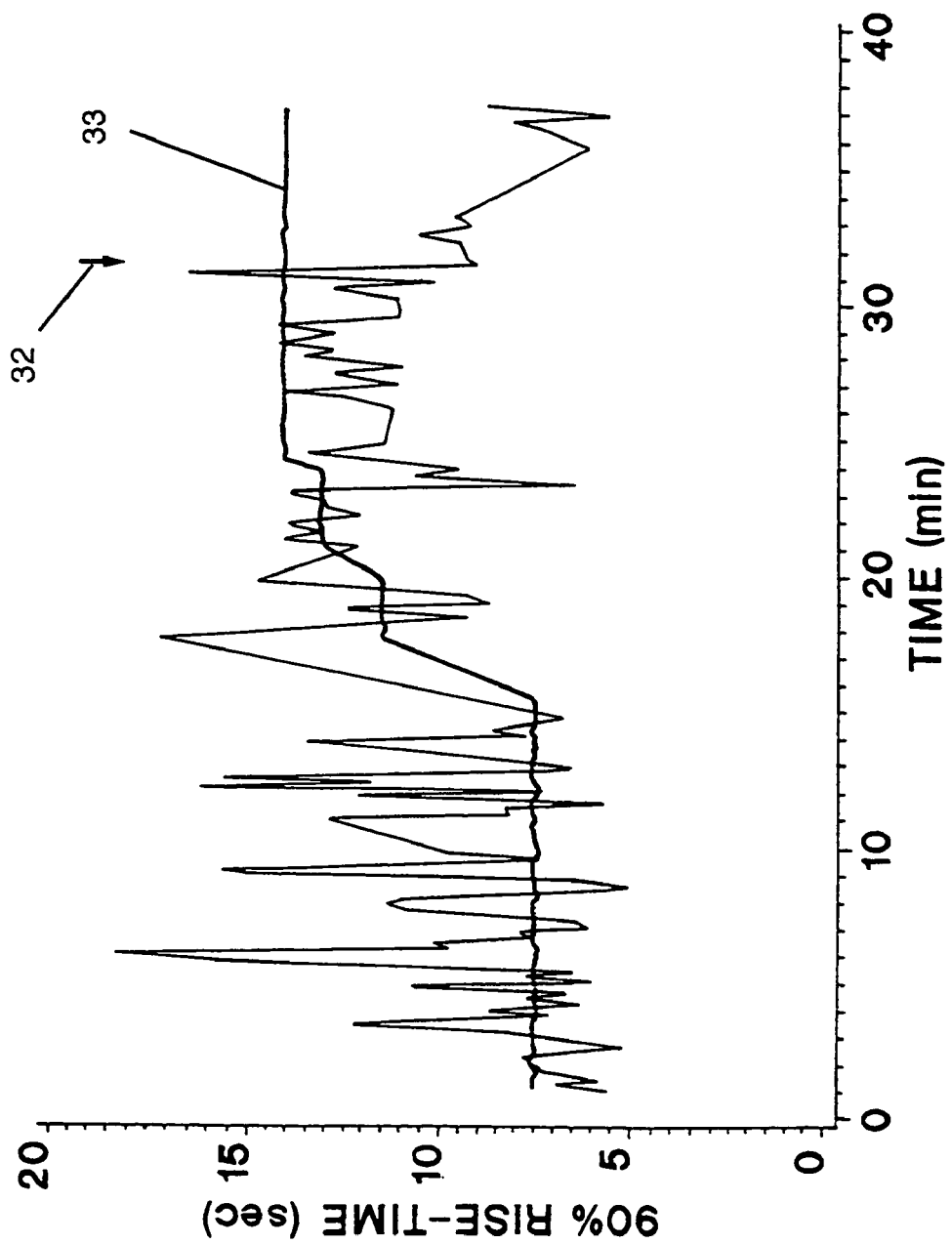
FIG. 7 represents the time course until 90% of the pressure plateau has been reached ("90% rise time") over the total period of an intervention, the mean value being visible at 33. Departing from a low value at the beginning of the intervention, a stepwise rise can be observed until a value that remains substantially constant upon termination of the intervention at 32 has been reached.
Figure 8:
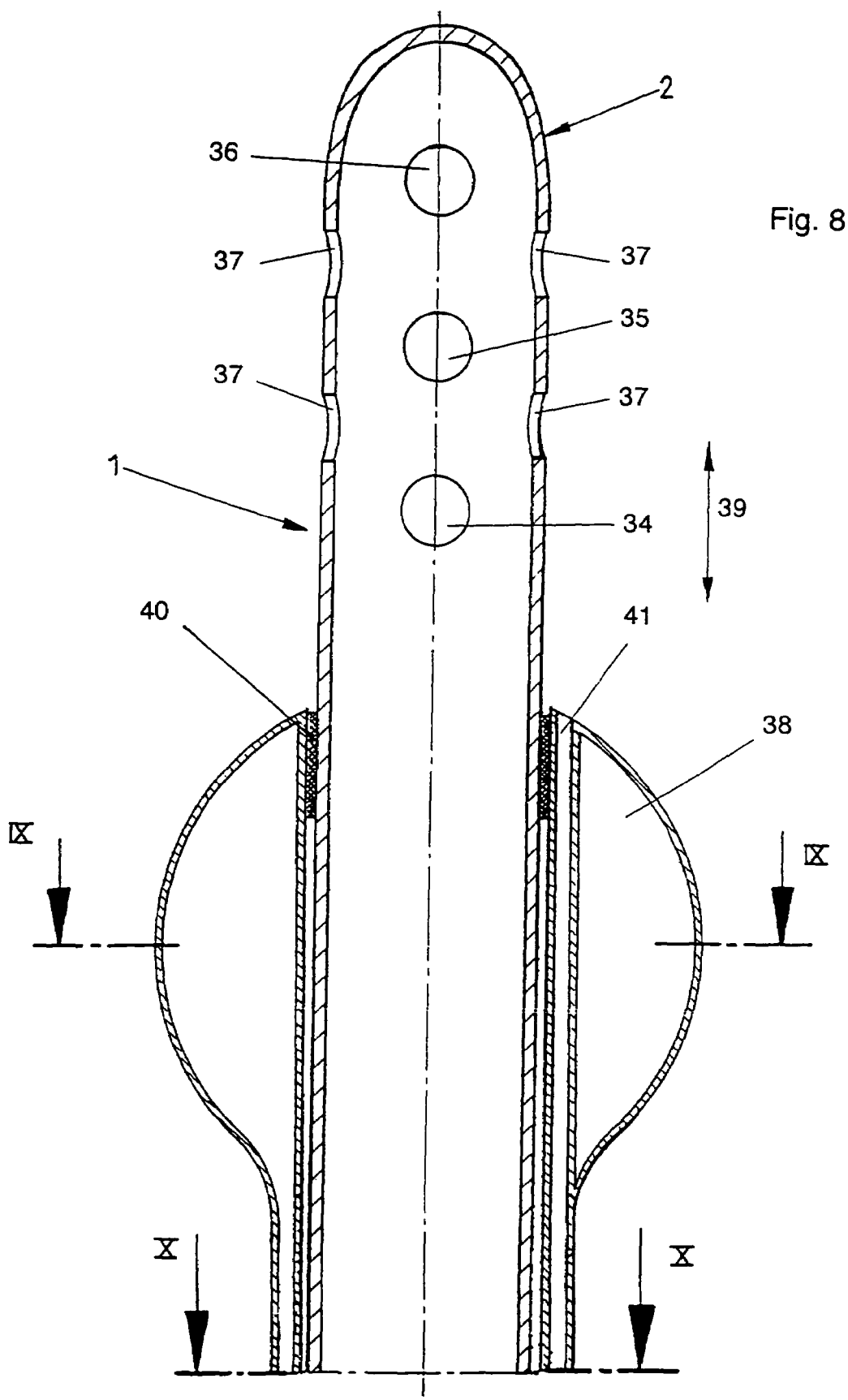
FIGS. 8 to 10 illustrate a multilumen balloon catheter to be used in connection with the method.

In FIG. 8, the distal end of a catheter 1 is denoted by 2. Depending on the number of lumina, different exit openings 34, 35, 36 or 37 may be connected with different lumina so as to render feasible the separate supply of pharmacologic substances or the supply of a perfusate in the same manner as, for instance, the determination of measured pressure values via the fluid column contained within a lumen. The distal end of the catheter 2 is sealingly guided in an expandable balloon 38 so as to be slidable in the sense of double arrow 39, the seal being denoted by 40. Furthermore, a further lumen 41 for pressure measurement is apparent.

After having reached a predetermined defined position of the balloon, the balloon 38 can be expanded, whereupon the respectively suitable position of the distal end 2, and of the exit openings or mouths 34, 35, 46 or 37, respectively, can be adjusted by the axial displacement of the distal end 2 relative to the balloon 38 in the sense of double arrow 39. If, with appropriately selected distances of the openings 34, 35, 36 or 37, the distal end is retracted in a manner that a portion of the mouths or openings is sealingly covered by the balloon, merely the free passages or openings 35, 36 or 37 will remain in direct contact with the surrounding fluid and, in particular, the blood within the blood circulation of a blood vessel.

Figure 9:
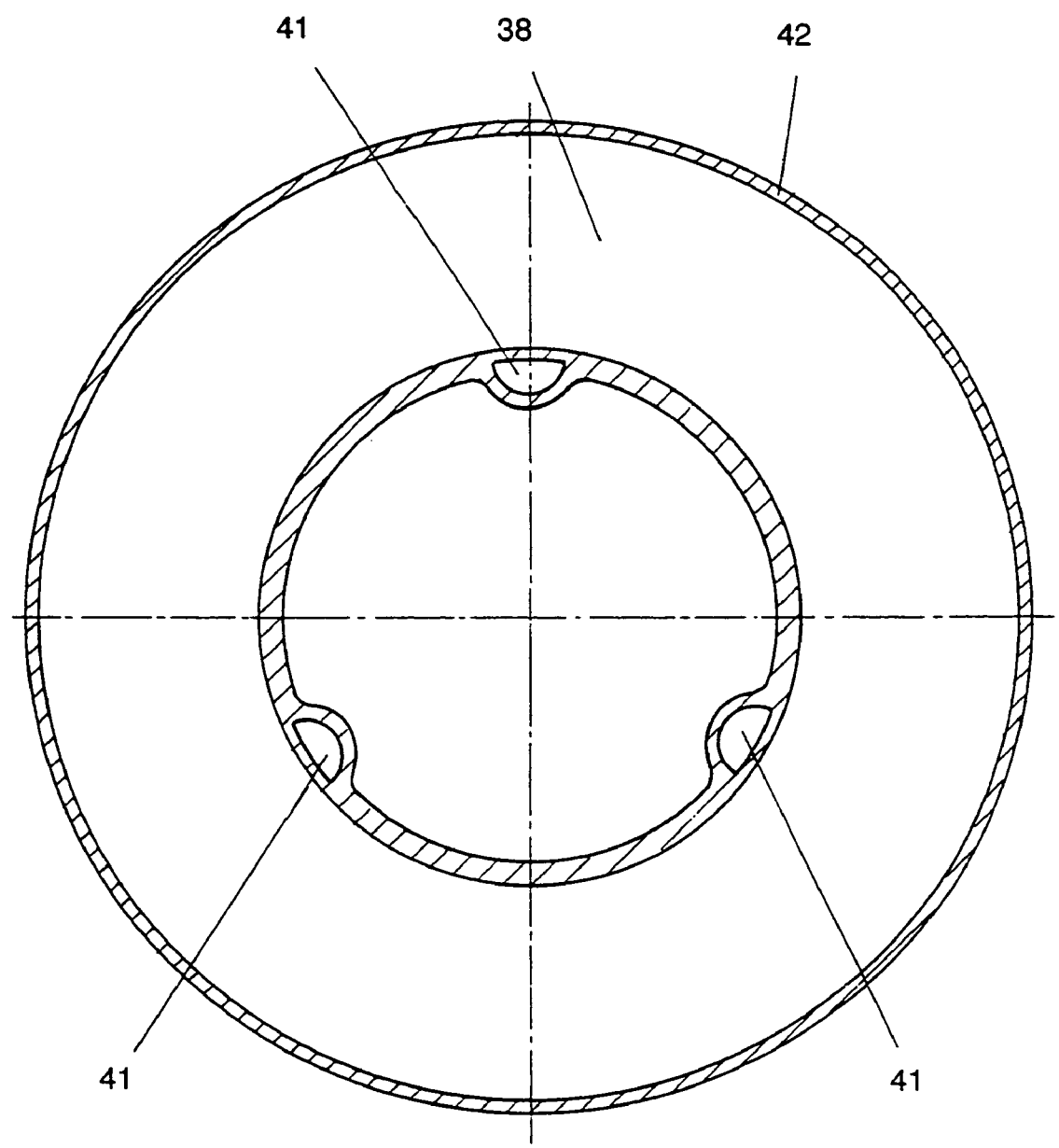

The illustration according to FIG. 9 merely shows the balloon 38, whose skin is denoted by 42. The inner wall, which is located adjacent to the displaceable part of the catheter, carries axial lumina 41 via which measured pressure values can, for instance, be obtained. One or several of such axial channels 41 may also serve to feed the pressure fluid for the expansion of the balloon 38.

Figure 10:
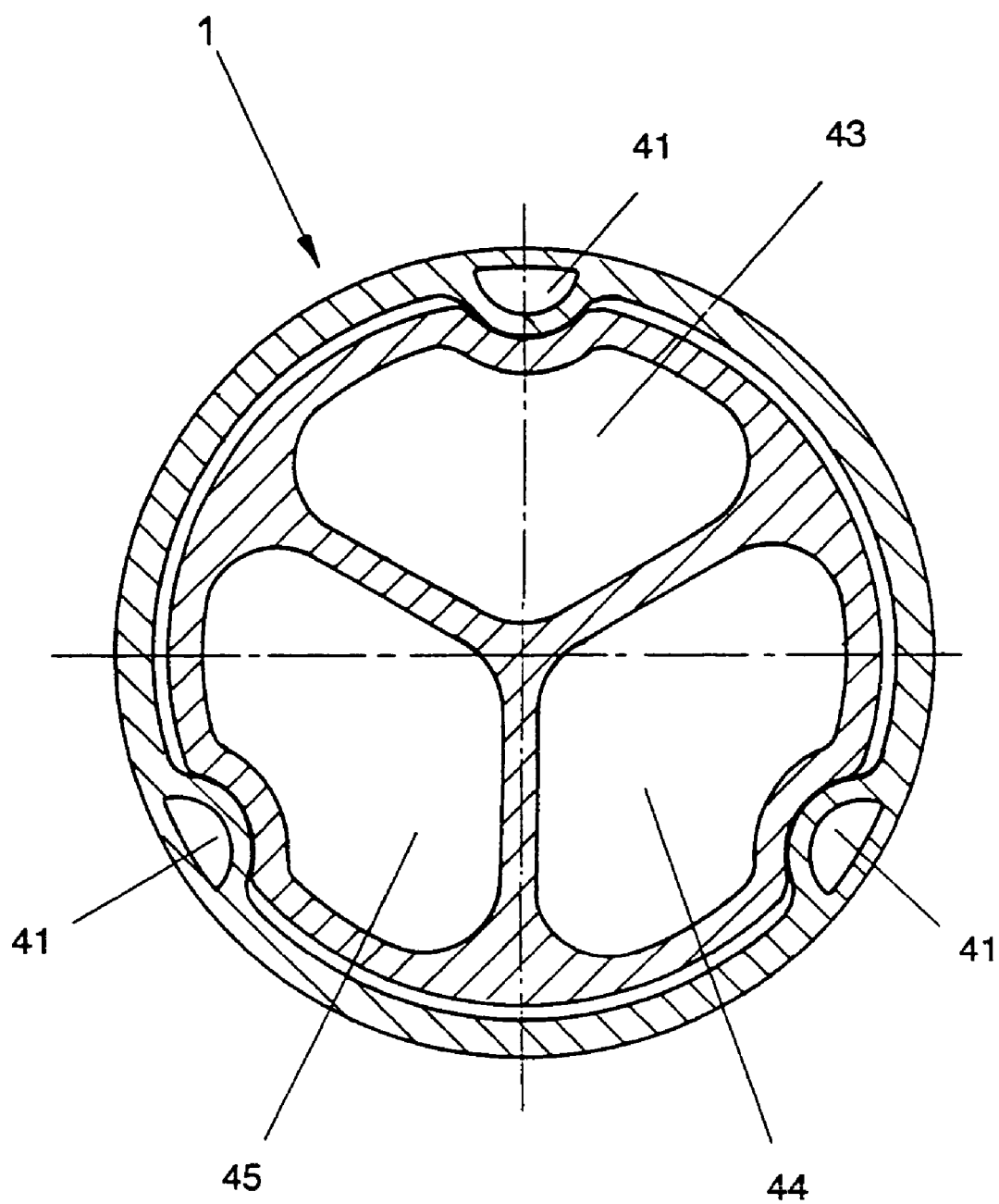

The illustration according to FIG. 10 depicts a multilumen catheter 1 whose individual lumina are denoted by 43, 44 and 45. The individual lumina may be connected with different mouths or openings 34, 35, 36 or 37, respectively, as are apparent from FIG. 8, wherein it is also feasible to arrange wires for the electric contacting of measuring sensors in such lumina.

The invention claimed is:

1. A method for intermittent occlusion of a coronary sinus comprising:
   occluding the coronary sinus with an occlusion device;
   continuously measuring the fluid pressure in the occluded coronary sinus and defining measured pressure values;
   releasing the occlusion of the coronary sinus as a function of at least one parameter derived from the measured pressure values;
   introducing a perfusate into the occluded coronary sinus or at least a vein running into the coronary sinus; and
   controlling an amount of perfusate introduced as a function of at least one of a local maximum and local minimum, each occurring within a heartbeat, of a derivative of a fluid pressure curve according to time.

2. A method according to claim 1, wherein at least one of a plateau value of local maxima, and a plateau value of local minima, of the derivative of the fluid pressure curve according to time are chosen as said parameter derived from the measured pressure values.

3. A method according to claim 1, wherein at least one of local maxima, or plateau values thereof, and local minima, or plateau values thereof, of the derivative of the fluid pressure curve according to time are compared with a set value.

4. A method according to claim 1, wherein either blood or a nutritive fluid is used as said perfusate.

5. A method according to claim 4, wherein the perfusate is arterial blood.

6. A method according to claim 1, wherein the perfusate is supplemented with pharmaceuticals.

7. A method according to claim 1, wherein the perfusate is directly introduced into the region of the vessels to be activated.

8. A method according to claim 1, wherein the fluid pressure in an arterial heart vessel is additionally measured and the control of the introduced amount of perfusate is effected by additionally considering the arterial pressure values measured.

9. A method for intermittent occlusion of a coronary sinus comprising:
occluding the coronary sinus with an occlusion device;
continuously measuring the fluid pressure in the occluded coronary sinus and defining measured pressure values;
releasing the occlusion of the coronary sinus as a function of at least one parameter derived from the measured pressure values;
introducing a perfusate into the occluded coronary sinus or at least a vein running into the coronary sinus; and
controlling an amount of perfusate introduced as a function of at least one of a plateau value of pressure minima and a plateau value of pressure maxima of consecutive heartbeats that is computationally estimated from the measured pressure values.

10. A method according to claim 9, wherein a difference of the plateau values of the pressure minima and pressure maxima is calculated and the amount of perfusate introduced is raised until the difference remains constant or increases.

11. A method according to claim 9, wherein the pressure maxima of consecutive heartbeats are compared with the plateau value of the pressure maxima and the occlusion of the coronary sinus is released upon reaching of a predetermined percentage of the plateau value of the pressure maxima.

12. A method according to claim 11, wherein the predetermined percentage is between 70% and 98%.

13. A method according to claim 9, wherein either blood or a nutritive fluid is used as said perfusate.

14. A method according to claim 13, wherein the perfusate is arterial blood.

15. A method according to claim 9, wherein the perfusate is supplemented with pharmaceuticals.

16. A method according to claim 9, wherein the perfusate is directly introduced into the region of the vessels to be activated.

17. A method according to claim 9, wherein the fluid pressure in an arterial heart vessel is additionally measured and the control of the introduced amount of perfusate is effected by additionally considering the arterial pressure values measured.

18. A device for intermittent occlusion of a coronary sinus, comprising:
an occlusion device to occlude the coronary sinus;
a controller to trigger or release an occlusion;
a pressure sensor to determine fluid pressure prevailing in the coronary sinus during the occlusion;
a duct structured to be introduced into the coronary sinus or a vein running into the coronary sinus, said duct being configured to be charged with a perfusate; and
a perfusate pump connected with an automatic controller, wherein the pressure sensor comprises a memory for the measured pressure values and is connected with a computation unit for calculation of at least one parameter derived from said measured pressure values, wherein control of an introduced amount of perfusate is performed under consideration of said parameter derived from the measured pressure values, and wherein the pressure sensor comprises a memory for local maxima of the measured pressure values and the computation unit comprises an evaluation circuit to computationally estimate a plateau value of pressure maxima of consecutive heartbeats and to cooperate with the pump for the control of the introduced amount of perfusate as a function of the plateau value of the pressure maxima.

19. A device according to claim 18, wherein the computation unit comprises a comparator circuit to compare the plateau values of pressure minima and pressure maxima and to cooperate with the pump for the control of the introduced amount of perfusate as a function of the difference between the pressure maxima and pressure minima, whereby the amount of perfusate introduced is raised as long as the difference remains constant or increases.

20. A device according to claim 18, wherein the automatic controller is connected with the controller to trigger or release the occlusion by the occlusion device, wherein the occlusion is released as pressure maxima of consecutive heartbeats have reached a predetermined percentage of the plateau value of the pressure maxima.

21. A device according to claim 20, wherein the predetermined percentage is larger than 70% and smaller than 98%.

22. A device according to claim 18, wherein the evaluation circuit performs a computational estimation of the plateau values by insertion of the pressure maxima or minima into an exponential curve.

23. A device according to claim 18, wherein the controller comprises the automatic controller for at least one of the pump and the computation unit.

24. A device according to claim 18, wherein the duct to be charged with a perfusate is arranged to be displaceable relative to the occlusion device and structured to be pushed forward directly into a region of vessels to be activated.

25. A device according to claim 18, further comprising an additional pressure measuring sensor provided to determine fluid pressure in an arterial heart vessel, the additional pressure sensor being connected with the computation unit, whereby the control of the introduced amount of perfusate is effected under additional consideration of the arterial pressure values measured.

26. A device for intermittent occlusion of a coronary sinus, comprising:
an occlusion device to occlude the coronary sinus;
a controller to trigger or release an occlusion;
a pressure sensor to determine fluid pressure prevailing in the coronary sinus during the occlusion;
a duct structured to be introduced into the coronary sinus or a vein running into the coronary sinus, said duct being configured to be charged with a perfusate; and
a perfusate pump connected with an automatic controller, wherein the pressure sensor comprises a memory for the measured pressure values and is connected with a computation unit to calculate at least one parameter derived from said measured pressure values, wherein control of an introduced amount of perfusate is performed under consideration of said parameter derived from the measured pressure values, wherein the measured pressure values stored in the memory are assigned time stamps, and wherein the memory is connected with the computation unit to calculate a derivative of the fluid pressure curve with respect to time, and wherein the computation unit comprises a comparator circuit to determine at least one of a local maximum and a local minimum, each occurring within a heartbeat, of the derivative of the fluid pressure curve with respect to time, whereby control of the introduced amount of perfusate is performed as a function of at least one of the local maxima and local minima.

27. A device according to claim 26, wherein the computation unit comprises a comparator circuit for the comparison of at least one of local maxima, or plateau values thereof, and local minima, or plateau values thereof, of the derivative of the fluid pressure curve with respect to time with a stored set value.

28. A device according to claim 26, wherein the computation unit comprises an evaluation circuit which computationally estimates at least one of a plateau value of local pressure maxima and local pressure minima of the derivative of the fluid pressure curve with respect to time and cooperates with the pump for the control of the introduced amount of perfusate as a function of the plateau value.

29. A device according to claim 28, wherein the evaluation circuit performs a computational estimation of the plateau values by insertion of the pressure maxima or minima into an exponential curve.

30. A device according to claim 26, wherein the pressure sensor comprises a memory for local maxima of the measured pressure values and the computation unit comprises an evaluation circuit computationally estimating a plateau value of pressure maxima of consecutive heartbeats and cooperates with the pump for the control of the introduced amount of perfusate as a function of the plateau value of the pressure maxima.

31. A device according to claim 30, wherein the computation unit comprises a comparator circuit to compare the plateau values of pressure minima and pressure maxima and to cooperate with the pump for the control of the introduced amount of perfusate as a function of the difference between the pressure maxima and pressure minima, whereby the amount of perfusate introduced is raised as long as the difference remains constant or increases.

32. A device according to claim 30, wherein the evaluation circuit performs a computational estimation of the plateau values by insertion of the pressure maxima or minima into an exponential curve.

33. A device according to claim 26, wherein the automatic controller is connected with the controller to trigger or release the occlusion by the occlusion device, wherein the occlusion is released as pressure maxima of consecutive heartbeats have reached a predetermined percentage of the plateau value of pressure maxima.

34. A device according to claim 33, wherein the predetermined percentage is larger than 70% and smaller than 98%.

35. A device according to claim 26, wherein the controller comprises the automatic controller for at least one of the pump and the computation unit.

36. A device according to claim 26, wherein the duct to be charged with a perfusate is arranged to be displaceable relative to the occlusion device and structured to be pushed forward directly into a region of vessels to be activated.

37. A device according to claim 26, further comprising an additional pressure measuring sensor to determine fluid pressure in an arterial heart vessel, the additional pressure sensor being connected with the computation unit, whereby the control of the introduced amount of perfusate is effected under additional consideration of the arterial pressure values measured.

* * * * *